(12) United States Patent (10) Patent No.: US 8,389,767 B2
Stoller et al. (45) Date of Patent: Mar. 5, 2013

(54) PROCESSES AND COMPOUNDS

(75) Inventors: Andre Denis Stoller, Stein (CH); Pierre Joseph Marcel Jung, Stein (CH); Christopher Richard Ayles Godfrey, Stein (CH); Peter Maienfisch, Stein (CH); Werner Zambach, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 386 days.

(21) Appl. No.: 12/676,078

(22) PCT Filed: Sep. 2, 2008

(86) PCT No.: PCT/EP2008/007160
§ 371 (c)(1),
(2), (4) Date: Mar. 2, 2010

(87) PCT Pub. No.: WO2009/030457
PCT Pub. Date: Mar. 12, 2009

(65) Prior Publication Data
US 2010/0204504 A1 Aug. 12, 2010

(30) Foreign Application Priority Data

Sep. 4, 2007 (GB) .................................. 0717189.5

(51) Int. Cl.
*C07C 233/75* (2006.01)
*C07D 213/81* (2006.01)
(52) U.S. Cl. ........ 564/184; 546/309; 544/297; 544/322; 544/333; 544/405; 544/406; 544/407
(58) Field of Classification Search .......................... None
See application file for complete search history.

(56) References Cited

FOREIGN PATENT DOCUMENTS

| AT | 213556 B | 2/1961 |
|---|---|---|
| DE | 1117135 B | 11/1961 |
| EP | 1661886 | 5/2006 |
| GB | 881510 | 11/1961 |

OTHER PUBLICATIONS

Shimano, Yasuo et al.: "Preparation of AB Polyacylthioureas and Related Copolyacylthioureas" Journal of Polymer Science, Polymer Chemistry Edition, 21(5), 1331-45 CODEN, 1983.
Lorenz, Guenther et al: "New Synthesis of Aromatic Polyamides" Makromolekulare Chemie, 130, 55-64 CODEN, 1969.

Primary Examiner — Michael Barker
(74) Attorney, Agent, or Firm — R. Kody Jones

(57) ABSTRACT

The invention relates to methods of using certain compounds of formula (I), (II) and (III) in the synthesis of an insecticide intermediate of formula (IV), wherein the substituents are as defined in claim 1, to processes for preparing these compounds, to processes which use these compounds to prepare insecticide intermediates, and to certain novel compounds of formula (II') and (III').

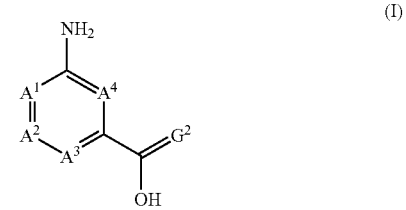

(I)

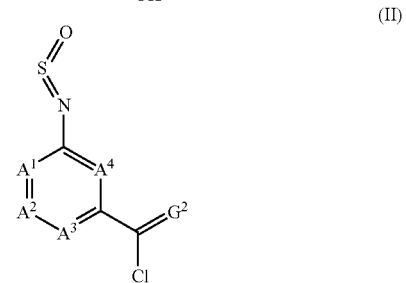

(II)

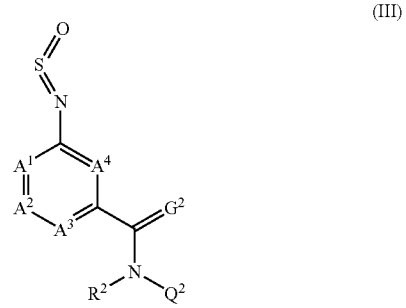

(III)

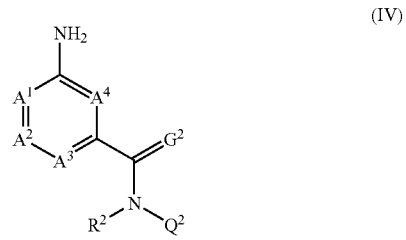

(IV)

11 Claims, No Drawings

PROCESSES AND COMPOUNDS

This application is a 371 of International Application No. PCT/EP2008/007160 filed Sep. 2, 2008, which claims priority to GB 0717189.5 filed Sep. 4, 2007, the contents of which are incorporated herein by reference.

The present invention relates to methods of using certain compounds of formula (I), (II) and (III) as intermediates, to processes for preparing these compounds, to processes which use these compounds to prepare insecticide intermediates of formula (IV), and to certain novel compounds of formula (II') and (III').

The compounds of the present invention are intermediates which are suitable for the synthesis of carbamate insecticides as disclosed, for example, in EP 1661886 and JP 2006225340, and for the synthesis of bisamide insecticides as disclosed, for example, in EP 1714958, JP 2006/306771, EP 1911751, EP 1916236, and WO 07/017,075.

Processes to carbamate insecticides and bisamide insecticides and some suitable intermediates, such as 3-amino-N-[2,6-dimethyl-4-(1,2,2,2-tetrafluoro-1-trifluoromethyl-ethyl)-phenyl]-benzamide and other 3-amino-benzamides, have been disclosed in EP 1661886, JP 2006225340, EP 1714958, JP 2006/306771, EP 1911751, EP 1916236, and WO 07/017,075. In these references, 3-amino-N-[2,6-dimethyl-4-(1,2,2,2-tetrafluoro-1-trifluoromethyl-ethyl)-phenyl]-benzamide was made as follows:

a) 3-nitro-benzoic acid was converted to 3-nitro-benzoyl chloride,
b) 3-nitro-benzoyl chloride was reacted with an aniline, that is 2,6-dimethyl-4-(1,2,2,2-tetrafluoro-1-trifluoromethyl-ethyl)-phenylamine, to form a 3-nitro-benzamide, that is 3-nitro-N-[2,6-dimethyl-4-(1,2,2,2-tetrafluoro-1-trifluoromethyl-ethyl)-phenyl]-benzamide, and
c) the 3-nitro-benzamide, that is 3-nitro-N-[2,6-dimethyl-4-(1,2,2,2-tetrafluoro-1-trifluoromethyl-ethyl)-phenyl]-benzamide, was reduced to afford the desired 3-amino-benzamide, that is 3-amino-N-[2,6-dimethyl-4-(1,2,2,2-tetrafluoro-1-trifluoromethyl-ethyl)-phenyl]-benzamide. Further 3-amino-benzamides were made, for example, by using a substituted 3-nitro-benzoic acid, such as 2-fluoro-3-nitro-benzoic acid, in step a) and/or a different aniline, such as 2-ethyl-6-methyl-4-(1,2,2,2-tetrafluoro-1-trifluoro-methyl-ethyl)-phenylamine, in step b). Whilst this three step synthesis gives satisfactory results in the laboratory a shorter route to 3-amino-benzamides is required if the carbamate insecticides or bisamide insecticides are to be manufactured on a commercial scale.

There is a need for new and better processes to bisamide insecticides and intermediates and this need is met by the present intermediates and the associated reactions. The present invention provides an alternative three step synthesis and a shorter two step synthesis which is more suitable for the manufacture of the carbamate insecticides or bisamide insecticides on a commercial scale. These syntheses avoid the need for reactions with disadvantageous features (e.g. expensive reagents are disadvantageous on account of costs, reactions which require a gas, such as hydrogen gas, are disadvantageous on account of safety, reactions with require a heavy metal, such as tin(II) chloride, are disadvantageous on account of (eco)toxicity. Instead these synthetic routes provide for the synthesis of the intermediates using reactions with advantageous features (e.g. sulfonyl chloride is an inexpensive reagent, no gas or heavy metal is required).

The present invention therefore provides a method of using as an intermediate in the production of a compound of formula (IV)

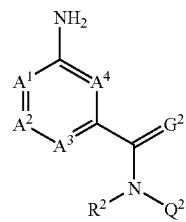

(IV)

wherein
$A^1, A^2, A^3$ and $A^4$ are independently of one another C—$R^3$ or nitrogen, provided that no more than two of $A^1, A^2, A^3$ and $A^4$ are nitrogen;
$R^2$ is hydrogen, $C_1$-$C_4$alkyl or $C_1$-$C_4$alkylcarbonyl-;
$G^2$ is oxygen or sulfur;
each $R^3$ is independently hydrogen, halogen, cyano, nitro, $C_1$-$C_4$alkyl, $C_1$-$C_4$haloalkyl, hydroxy, $C_1$-$C_4$alkoxy-, $C_1$-$C_4$haloalkoxy-, thiol, $C_1$-$C_4$alkylthio-, $C_1$-$C_4$haloalkylthio-, $C_1$-$C_4$alkylsulfinyl-, $C_1$-$C_4$haloalkylsulfinyl-, $C_1$-$C_4$alkylsulfonyl-, $C_1$-$C_4$haloalkylsulfonyl-, amino, N—$C_1$-$C_4$alkylamino- or N,N-di-($C_1$-$C_4$alkyl)-amino-; and
$Q^2$ is a moiety of formula (A) or (B)

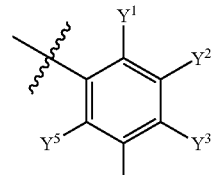

(A)

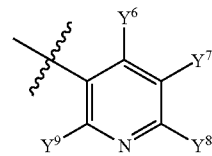

(B)

wherein
$Y^1$ and $Y^5$ are independently of each other halogen, cyano, thiocyanato, $C_1$-$C_4$alkyl, $C_1$-$C_4$haloalkyl, $C_1$-$C_4$alkoxy-$C_1$-$C_4$-alkyl-, cyano-$C_1$-$C_4$-alkyl-, $C_1$-$C_3$alkylthio-, $C_1$-$C_3$haloalkylthio-, $C_1$-$C_3$alkylsulfinyl-, $C_1$-$C_3$haloalkylsulfinyl-, $C_1$-$C_3$alkylsulfonyl- or $C_1$-$C_3$haloalkylsulfonyl-;
$Y^3$ is $C_2$-$C_6$perfluoroalkyl, $C_1$-$C_6$perfluoroalkylthio-, $C_1$-$C_6$perfluoroalkylsulfinyl- or $C_1$-$C_6$perfluoroalkylsulfonyl-;
$Y^2$ and $Y^4$ are independently of each other hydrogen, halogen or $C_1$-$C_4$alkyl;
$Y^6$ and $Y^9$ are independently of each other halogen, cyano, thiocyanato, $C_1$-$C_4$alkyl, $C_1$-$C_4$haloalkyl, $C_1$-$C_4$alkoxy-$C_1$-$C_4$-alkyl-, cyano-$C_1$-$C_4$-alkyl-, $C_1$-$C_3$alkylthio-, $C_1$-$C_3$haloalkylthio-, $C_1$-$C_3$alkylsulfinyl-, $C_1$-$C_3$haloalkylsulfinyl-, $C_1$-$C_3$alkylsulfonyl- or $C_1$-$C_3$haloalkylsulfonyl-;
$Y^8$ is $C_1$-$C_4$haloalkoxy-, $C_2$-$C_6$perfluoroalkyl, $C_1$-$C_6$perfluoroalkylthio-, $C_1$-$C_6$perfluoroalkylsulfinyl- or $C_1$-$C_6$ perfluoroalkylsulfonyl-;
$Y^7$ is hydrogen, halogen or $C_1$-$C_4$alkyl;
or an N-oxide or a salt thereof;

a) a compound of formula (I)

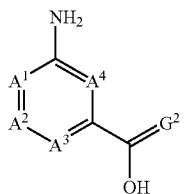

wherein $A^1$, $A^2$, $A^3$, $A^4$ and $G^2$ are as defined for a compound of formula (IV); or an N-oxide or a salt thereof; or b) a compound of formula (II)

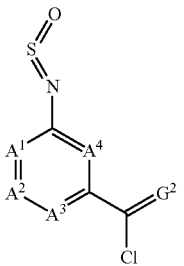

wherein $A^1$, $A^2$, $A^3$, $A^4$ and $G^2$ are as defined for a compound of formula (IV); or an N-oxide or a salt thereof; or c) a compound of formula (III)

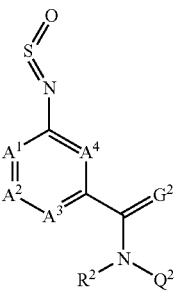

wherein $A^1$, $A^2$, $A^3$, $A^4$, $R^2$, $G^2$ and $Q^2$ are as defined for a compound of formula (IV); or an N-oxide or a salt thereof.

The compounds of formula (I), (II), (III) and (IV) may exist in different geometric or optical isomers or tautomeric forms. This invention covers all such isomers and tautomers and mixtures thereof in all proportions as well as isotopic forms such as deuterated compounds.

Each alkyl moiety either alone or as part of a larger group (such as alkoxy, alkylcarbonyl, alkoxycarbonyl) is a straight or branched chain and is, for example, methyl, ethyl, n-propyl, prop-2-yl, n-butyl, but-2-yl, 2-methyl-prop-1-yl or 2-methyl-prop-2-yl. The alkyl groups are preferably $C_1$ to $C_6$ alkyl groups, more preferably $C_1$-$C_4$, most preferably $C_1$-$C_3$ alkyl groups.

Halogen is fluorine, chlorine, bromine or iodine.

Haloalkyl groups (either alone or as part of a larger group, such as haloalkoxy or haloalkylthio) are alkyl groups which are substituted by one or more of the same or different halogen atoms and are, for example, trifluoromethyl, chlorodifluoromethyl, 2,2,2-trifluoro-ethyl, or 2,2-difluoro-ethyl. Perfluoroalkyl groups (either alone or as part of a larger group, such as perfluoroalkylthio) are a particular type of haloalkyl group; they are alkyl groups which are completely substituted with fluorine atoms and are, for example, trifluoromethyl, pentafluoroethyl, heptafluoro-prop-2-yl, or nonafluoro-but-2-yl.

Cyanoalkyl groups are alkyl groups which are substituted with one or more cyano groups, for example, cyanomethyl or 1,3-dicyanopropyl.

Preferred groups for $A^1$, $A^2$, $A^3$, $A^4$, $R^2$, $G^2$, $R^3$, and $Q^2$ in any combination thereof are set out below. The preferences apply to compounds of formula (I), (II), (III) and (IV), respectively.

Preferably $A^1$ is C—$R^3$.
Preferably $A^2$ is C—$R^3$.
Preferably $A^3$ is C—$R^3$.
Preferably $A^4$ is C—$R^3$.
Preferably $R^2$ is hydrogen, methyl, ethyl or acetyl, more preferably hydrogen, methyl or ethyl, even more preferably hydrogen or ethyl, most preferably hydrogen.

Preferably $G^2$ is oxygen.

Preferably each $R^3$ is independently hydrogen, halogen, cyano, nitro, $C_1$-$C_4$alkyl, $C_1$-$C_4$haloalkyl or $C_1$-$C_4$alkoxy-, more preferably hydrogen, halogen, cyano, nitro, methyl, trifluoromethyl or methoxy-, even more preferably hydrogen, fluoro, cyano, nitro, trifluoromethyl or methoxy-, yet even more preferably hydrogen, fluoro or cyano, most preferably hydrogen.

Preferably $Q^2$ is a moiety of formula (A).

Preferably $Y^3$ is halogen, cyano, methyl, ethyl, trifluoromethyl or methoxymethyl-, more preferably bromo, chloro, methyl, ethyl or methoxymethyl-, even more preferably bromo, methyl or ethyl, most preferably methyl.

Preferably $Y^2$ is hydrogen, chloro, fluoro or methyl, most preferably hydrogen.

Preferably $Y^3$ is heptafluoropropyl, heptafluoroprop-2-yl, heptafluoropropylthio-, heptafluoropropylsulfinyl-, heptafluoropropylsulfonyl-, heptafluoroprop-2-ylthio-, heptafluoroprop-2-ylsulfinyl-, heptafluoroprop-2-ylsulfonyl- or nonafluorobut-2-yl, more preferably heptafluoroprop-2-yl or nonafluorobut-2-yl, most preferably heptafluoroprop-2-yl.

Preferably $Y^4$ is hydrogen, chloro, fluoro or methyl, most preferably hydrogen.

Preferably $Y^5$ is halogen, cyano, methyl, ethyl or trifluoromethyl, more preferably bromo, chloro, methyl or ethyl, even more preferably bromo, methyl or ethyl, most preferably methyl.

Preferably $Y^6$ is halogen, cyano, methyl, ethyl, trifluoromethyl or methoxymethyl-, more preferably bromo, chloro, methyl, ethyl or methoxymethyl-, even more preferably bromo, methyl or ethyl, most preferably methyl.

Preferably $Y^7$ is hydrogen, chloro, fluoro or methyl, most preferably hydrogen.

Preferably $Y^8$ is heptafluoropropyl, heptafluoroprop-2-yl, heptafluoropropylthio-, heptafluoropropylsulfinyl-, heptafluoropropylsulfonyl-, heptafluoroprop-2-ylthio-, heptafluoroprop-2-ylsulfinyl-, heptafluoroprop-2-ylsulfonyl- or nonafluorobut-2-yl, more preferably heptafluoroprop-2-yl or nonafluorobut-2-yl, most preferably heptafluoroprop-2-yl.

Preferably $Y^9$ is halogen, cyano, methyl, ethyl, trifluoromethyl or methoxymethyl-, more preferably bromo, chloro, methyl, ethyl or methoxymethyl-, even more preferably bromo, methyl or ethyl, most preferably methyl.

In a preferred embodiment $A^1$, $A^2$, $A^3$, $A^4$ are CH.

In a preferred embodiment $A^1$ is C—F, and $A^2$, $A^3$, and $A^4$ are CH.

In a preferred embodiment $A^2$ is C—F, and $A^1$, $A^3$, and $A^4$ are CH.

In a preferred embodiment $A^3$ is C—F, and $A^1$, $A^2$, and $A^4$ are CH.

In a preferred embodiment $A^4$ is C—F, and $A^1$, $A^2$, and $A^3$ are CH.

In a preferred embodiment $A^1$ is C—CN, and $A^2$, $A^3$, and $A^4$ are CH.

In a preferred embodiment $A^2$ is C—CN, and $A^1$, $A^3$, and $A^4$ are CH.

In a preferred embodiment $A^3$ is C—CN, and $A^1$, $A^2$, and $A^4$ are CH.

In a preferred embodiment $A^4$ is C—CN, and $A^1$, $A^2$, and $A^3$ are CH.

In a preferred embodiment $A^1$ is C—$NO_2$, and $A^2$, $A^3$, and $A^4$ are CH.

In a preferred embodiment $A^2$ is C—$NO_2$, and $A^1$, $A^3$, and $A^4$ are CH.

In a preferred embodiment $A^3$ is C—$NO_2$, and $A^1$, $A^2$, and $A^4$ are CH.

In a preferred embodiment $A^4$ is C—$NO_2$, and $A^1$, $A^2$, and $A^3$ are CH.

In a preferred embodiment $Q^2$ is 2,6-dimethyl-4-(heptafluoroprop-2-yl)-phenyl.

In a preferred embodiment $Q^2$ is 2-ethyl-6-methyl-4-(heptafluoroprop-2-yl)-phenyl.

In a preferred embodiment $Q^2$ is 2,6-diethyl-4-(heptafluoroprop-2-yl)-phenyl.

In a preferred embodiment $Q^2$ is 2-methoxymethyl-6-methyl-4-(heptafluoroprop-2-yl)-phenyl.

In a preferred embodiment $Q^2$ is 2-bromo-6-methyl-4-(heptafluoroprop-2-yl)-phenyl.

In a preferred embodiment $Q^2$ is 2-bromo-6-ethyl-4-(heptafluoroprop-2-yl)-phenyl.

In a preferred embodiment $Q^2$ is 2,6-dichloro-4-(heptafluoroprop-2-yl)-phenyl.

In a preferred embodiment $Q^2$ is 2,6-dibromo-4-(heptafluoroprop-2-yl)-phenyl.

In a preferred embodiment $Q^2$ is 2,6-dimethyl-4-(nonafluorobut-2-yl)-phenyl.

In a preferred embodiment $Q^2$ is 2-ethyl-6-methyl-4-(nonafluorobut-2-yl)-phenyl.

In a preferred embodiment $Q^2$ is 2,6-diethyl-4-(nonafluorobut-2-yl)-phenyl.

In a preferred embodiment $Q^2$ is 2-methoxymethyl-6-methyl-4-(nonafluorobut-2-yl)-phenyl.

In a preferred embodiment $Q^2$ is 2-bromo-6-methyl-4-(nonafluorobut-2-yl)-phenyl.

In a preferred embodiment $Q^2$ is 2-bromo-6-ethyl-4-(nonafluorobut-2-yl)-phenyl.

In a preferred embodiment $Q^2$ is 2,6-dichloro-4-(nonafluorobut-2-yl)-phenyl.

In a preferred embodiment $Q^2$ is 2,6-dibromo-4-(nonafluorobut-2-yl)-phenyl.

Examples of compounds of formula (I) which illustrate the present invention are provided in Table 1.

TABLE 1

Table 1 provides 13 compounds of formula (I) wherein $G^2$ is oxygen and $X^1$, $X^2$, $X^3$ and $X^4$ have the values specified in Table 1.

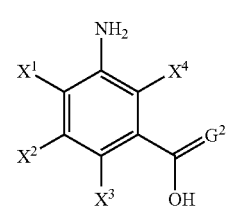

(I)

| Comp No. | $X^1$ | $X^2$ | $X^3$ | $X^4$ |
|---|---|---|---|---|
| 1.01 | H | H | H | H |
| 1.02 | —F | H | H | H |
| 1.03 | H | —F | H | H |
| 1.04 | H | H | —F | H |
| 1.05 | H | H | H | —F |
| 1.06 | —CN | H | H | H |
| 1.07 | H | —CN | H | H |
| 1.08 | H | H | —CN | H |
| 1.09 | H | H | H | —CN |
| 1.10 | —$NO_2$ | H | H | H |
| 1.11 | H | —$NO_2$ | H | H |
| 1.12 | H | H | —$NO_2$ | H |
| 1.13 | H | H | H | —$NO_2$ |

Examples of compounds of formula (II) which illustrate the present invention are provided in Table 2.

TABLE 2

Table 2 provides 13 compounds of formula (II) wherein $G^2$ is oxygen, and $X^1$, $X^2$, $X^3$ and $X^4$ have the values specified in Table 2.

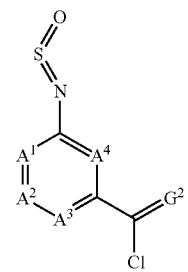

(II)

| Comp No. | $X^1$ | $X^2$ | $X^3$ | $X^4$ |
|---|---|---|---|---|
| 2.01 | H | H | H | H |
| 2.02 | —F | H | H | H |
| 2.03 | H | —F | H | H |
| 2.04 | H | H | —F | H |
| 2.05 | H | H | H | —F |
| 2.06 | —CN | H | H | H |
| 2.07 | H | —CN | H | H |
| 2.08 | H | H | —CN | H |
| 2.09 | H | H | H | —CN |
| 2.10 | —$NO_2$ | H | H | H |
| 2.11 | H | —$NO_2$ | H | H |
| 2.12 | H | H | —$NO_2$ | H |
| 2.13 | H | H | H | —$NO_2$ |

Examples of compounds of formula (III) which illustrate the present invention are provided in Table 3 to Table 18.

TABLE 3

Table 3 provides 13 compounds of formula (III) wherein $G^2$ is oxygen, $R^2$ is hydrogen and $Q^2$ is 2,6-dimethyl-4-(heptafluoroprop-2-yl)-phenyl, and $X^1$, $X^2$, $X^3$ and $X^4$ have the values specified in Table 3.

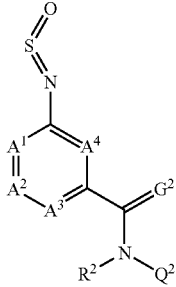

(III)

| Comp No. | $X^1$ | $X^2$ | $X^3$ | $X^4$ |
|---|---|---|---|---|
| 3.01 | H | H | H | H |
| 3.02 | —F | H | H | H |
| 3.03 | H | —F | H | H |
| 3.04 | H | H | —F | H |
| 3.05 | H | H | H | —F |
| 3.06 | —CN | H | H | H |
| 3.07 | H | —CN | H | H |
| 3.08 | H | H | —CN | H |
| 3.09 | H | H | H | —CN |
| 3.10 | —NO$_2$ | H | H | H |
| 3.11 | H | —NO$_2$ | H | H |
| 3.12 | H | H | —NO$_2$ | H |
| 3.13 | H | H | H | —NO$_2$ |

Table 4:

Table 4 provides 13 compounds of formula (III) wherein $G^2$ is oxygen, $R^2$ is hydrogen and $Q^2$ is 2-ethyl-6-methyl-4-(heptafluoroprop-2-yl)-phenyl, and $X^1$, $X^2$, $X^3$ and $X^4$ have the values specified in Table 3.

Table 5:

Table 5 provides 13 compounds of formula (III) wherein $G^2$ is oxygen, $R^2$ is hydrogen and $Q^2$ is 2,6-diethyl-4-(heptafluoroprop-2-yl)-phenyl, and $X^1$, $X^2$, $X^3$ and $X^4$ have the values specified in Table 3.

Table 6:

Table 6 provides 13 compounds of formula (III) wherein $G^2$ is oxygen, $R^2$ is hydrogen and $Q^2$ is 2-methoxymethyl-6-methyl-4-(heptafluoroprop-2-yl)-phenyl, and $X^1$, $X^2$, $X^3$ and $X^4$ have the values specified in Table 3.

Table 7:

Table 7 provides 13 compounds of formula (III) wherein $G^2$ is oxygen, $R^2$ is hydrogen and $Q^2$ is 2-bromo-6-methyl-4-(heptafluoroprop-2-yl)-phenyl, and $X^1$, $X^2$, $X^3$ and $X^4$ have the values specified in Table 3.

Table 8:

Table 8 provides 13 compounds of formula (III) wherein $G^2$ is oxygen, $R^2$ is hydrogen and $Q^2$ is 2-bromo-6-ethyl-4-(heptafluoroprop-2-yl)-phenyl, and $X^1$, $X^2$, $X^3$ and $X^4$ have the values specified in Table 3.

Table 9:

Table 9 provides 13 compounds of formula (III) wherein $G^2$ is oxygen, $R^2$ is hydrogen and $Q^2$ is 2,6-dichloro-4-(heptafluoroprop-2-yl)-phenyl, and $X^1$, $X^2$, $X^3$ and $X^4$ have the values specified in Table 3.

Table 10:

Table 10 provides 13 compounds of formula (III) wherein $G^2$ is oxygen, $R^2$ is hydrogen and $Q^2$ is 2,6-dibromo-4-(heptafluoroprop-2-yl)-phenyl, and $X^1$, $X^2$, $X^3$ and $X^4$ have the values specified in Table 3.

Table 11:

Table 11 provides 13 compounds of formula (III) wherein $G^2$ is oxygen, $R^2$ is hydrogen and $Q^2$ is 2,6-dimethyl-4-(nonafluorobut-2-yl)-phenyl, and $X^1$, $X^2$, $X^3$ and $X^4$ have the values specified in Table 3.

Table 12:

Table 12 provides 13 compounds of formula (III) wherein $G^2$ is oxygen, $R^2$ is hydrogen and $Q^2$ is 2-ethyl-6-methyl-4-(nonafluorobut-2-yl)-phenyl, and $X^1$, $X^2$, $X^3$ and $X^4$ have the values specified in Table 3.

Table 13:

Table 13 provides 13 compounds of formula (III) wherein $G^2$ is oxygen, $R^2$ is hydrogen and $Q^2$ is 2,6-diethyl-4-(nonafluorobut-2-yl)-phenyl, and $X^1$, $X^2$, $X^3$ and $X^4$ have the values specified in Table 3.

Table 14:

Table 14 provides 13 compounds of formula (III) wherein $G^2$ is oxygen, $R^2$ is hydrogen and $Q^2$ is 2-methoxymethyl-6-methyl-4-(nonafluorobut-2-yl)-phenyl, and $X^1$, $X^2$, $X^3$ and $X^4$ have the values specified in Table 3.

Table 15:

Table 15 provides 13 compounds of formula (III) wherein $G^2$ is oxygen, $R^2$ is hydrogen and $Q^2$ is 2-bromo-6-methyl-4-(nonafluorobut-2-yl)-phenyl, and $X^1$, $X^2$, $X^3$ and $X^4$ have the values specified in Table 3.

Table 16:

Table 16 provides 13 compounds of formula (III) wherein $G^2$ is oxygen, $R^2$ is hydrogen and $Q^2$ is 2-bromo-6-ethyl-4-(nonafluorobut-2-yl)-phenyl, and $X^1$, $X^2$, $X^3$ and $X^4$ have the values specified in Table 3.

Table 17:

Table 17 provides 13 compounds of formula (III) wherein $G^2$ is oxygen, $R^2$ is hydrogen and $Q^2$ is 2,6-dichloro-4-(nonafluorobut-2-yl)-phenyl, and $X^1$, $X^2$, $X^3$ and $X^4$ have the values specified in Table 3.

Table 18:

Table 18 provides 13 compounds of formula (III) wherein $G^2$ is oxygen, $R^2$ is hydrogen and $Q^2$ is 2,6-dibromo-4-(nonafluorobut-2-yl)-phenyl, and $X^1$, $X^2$, $X^3$ and $X^4$ have the values specified in Table 3.

Scheme A

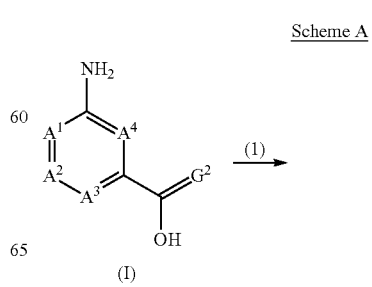

(I)

-continued

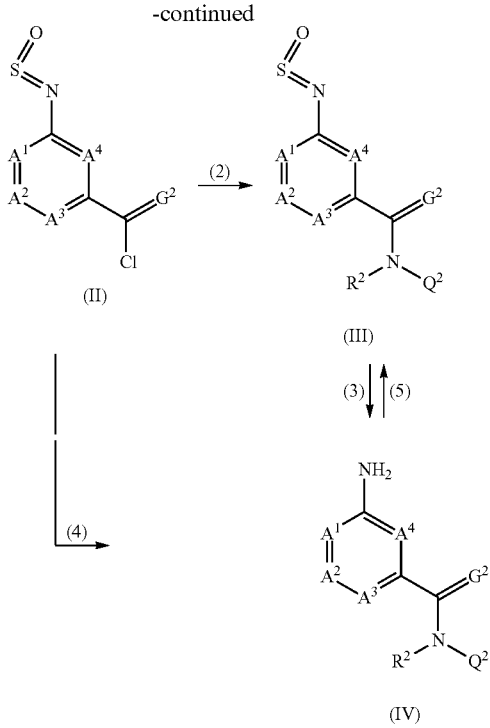

Scheme A summarizes reactions (1), (2), (3), (4) and (5) in which an insecticide intermediate of formula (II) is prepared from a compound of formula (I), an insecticide intermediate of formula (III) is prepared from a compound of formula (II), an insecticide intermediate of formula (IV) is prepared from a compound of formula (III), an insecticide intermediate of formula (IV) is prepared from a compound of formula (II), and an insecticide intermediate of formula (III) is prepared from a compound of formula (IV), respectively.

Reactions of type (1)

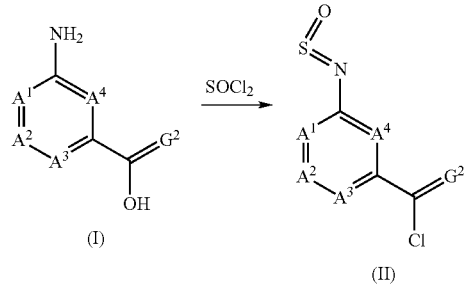

1) Acid chlorides of formula (II) may be made from an amino-carboxylic acid of formula (I) by methods known to a person skilled in the art, such as treatment with thionyl chloride. This reaction is described, for example, in Journal fuer Praktische Chemie (Leipzig) (1937), 148, 161-169. The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

Reactions of type (2)

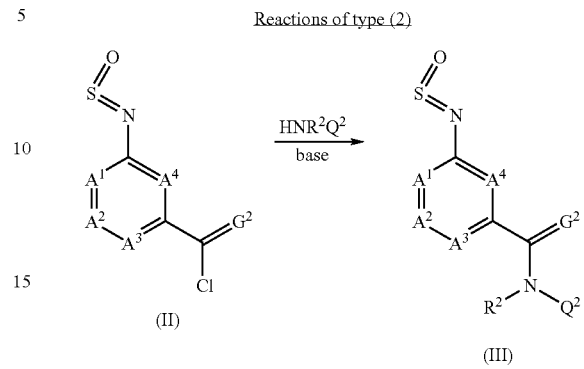

2) Compounds of formula (III) may be made by treatment of a compound of formula (II) by amide bond formation with an amine of formula $HNR^2Q^2$ under basic conditions (for example in the presence of an organic base such as pyridine, triethylamine, 4-(dimethylamino)-pyridine, diisopropylethylamine, or an excess of the amine $HNR^2Q^2$ or in the presence of an acid scavenger such as sodium carbonate, sodium hydrogen carbonate, potassium carbonate or potassium hydrogen carbonate). The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

Reactions of type (3)

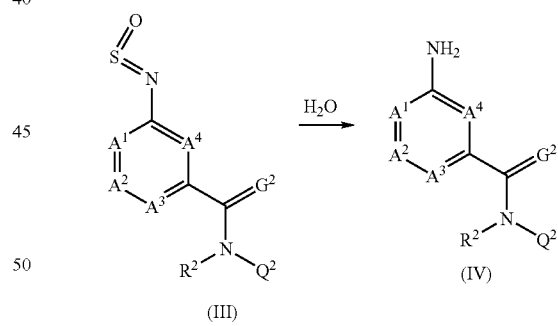

3) Compounds of formula (IV) may be made by treatment of a compound of formula (III) with water under neutral or acidic or basic conditions (preferably acidic conditions, for example in the presence of dilute aqueous hydrochloric acid). The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof (such as a mixture of dichloromethane and tetrahydrofuran).

Reactions of type (4)

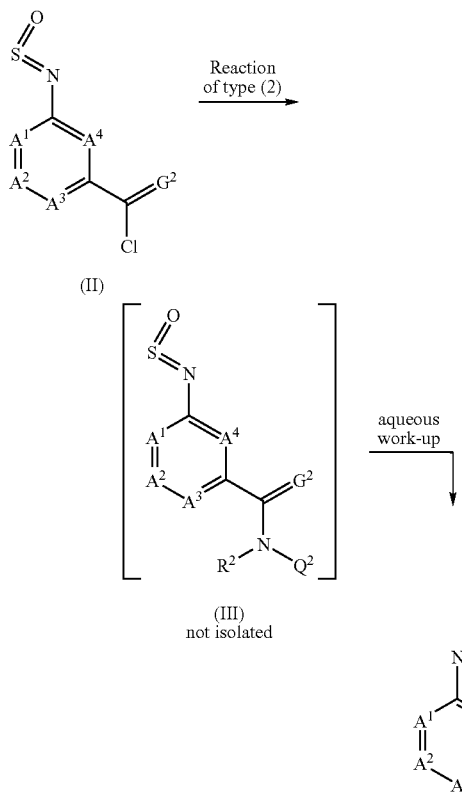

(II)

(III) not isolated (IV)

4) Reactions of type (4) are a combination of a reaction of type (2) with a reaction of type (3). As compounds of formula (III) can be sensitive towards hydrolysis, it is convenient not to isolate them but to directly transform them into compounds of formula (IV), which are usually easier to handle. Furthermore, this reduces the number of practical steps by one, as the last transformation can conveniently be achieved during the aqueous work-up of the reaction mixture to compounds of formula (III). The reaction of 3-sulfinylamino-benzoyl chloride with a primary amine is described, for example, in EP 54,839. The reaction of 3-sulfinylamino-benzoyl chloride with aniline, 2-methyl-aniline and 2-methoxy-aniline is described, for example, in Deposited Doc. (1975), (VINITI 2561-2575), (CAN 87:134385), The reaction of 2-sulfinylamino-benzoyl chloride with an aniline is described, for example, in Journal of Organic Chemistry (2001), 66(8), 2784-2788. However, none of these references discloses an intermediate of formula (III). It has now been demonstrated that a compound of formula (III) is the direct product of a type 2) reaction and that the compound of formula (III) is subsequently hydrolysed, for example, during aqueous work-up. The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

Reactions of type (5)

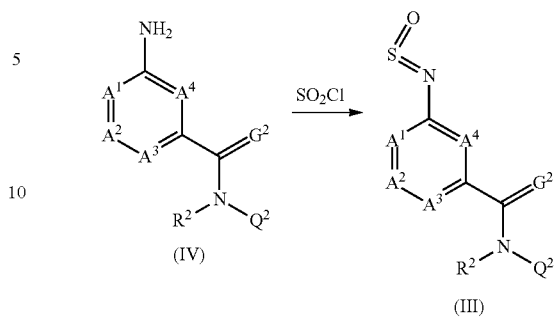

(IV)

(III)

5) Compounds of formula (III) may also be made by treatment of an amino-carboxylic acid derivative of formula (IV) by methods known to a person skilled in the art, such as treatment with thionyl chloride. The reaction can preferably be carried out in a suitable solvent, preferably an aprotic solvent, for example an ether (such as tetrahydrofuran or diethyl ether), a halogenated hydrocarbon (such as dichloromethane, chloroform, carbon tetrachloride, or 1,1,1-trichloroethane), a halogenated or non-halogenated aromatic (such as toluene or chlorobenzene), or a mixture thereof.

Certain compounds of formula (II) and (III) are novel and as such form a further aspect of the invention. The present invention therefore provides a compound of formula (II')

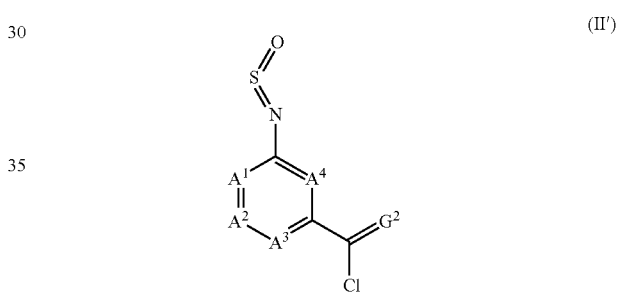

(II')

wherein
$A^1$, $A^2$, $A^3$, $A^4$ and $G^2$ are as defined for a compound of formula (I); or an N-oxide or a salt thereof, provided that (II') is not 2-chloro-5-sulfinylamino-benzoyl chloride, 4-methoxy-3-sulfinylamino-benzoyl chloride, 4-methyl-3-sulfinylamino-benzoyl chloride, 3-sulfinylamino-benzoyl chloride, 2,3,4,6-tetraiodo-5-sulfinylamino-benzoyl chloride or 2,4,6-triiodo-3-sulfinylamino-benzoyl chloride. The preferences for $A^1$, $A^2$, $A^3$, $A^4$ and $G^2$ are the same as the preferences set out for the corresponding substituents of a compound of formula (I).

Furthermore, the present invention provides a compound of formula (III')

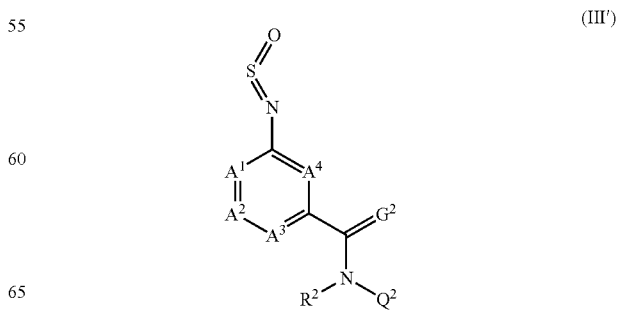

(III')

wherein
A¹, A², A³, A⁴ and G² are as defined for a compound of formula (I); and
R² and Q² are as defined for a compound of formula (III); or an N-oxide or a salt thereof. The preferences for A¹, A², A³, A⁴ and G² are the same as the preferences set out for the corresponding substituents of a compound of formula (I). The preferences for R² and Q² are the same as the preferences set out for the corresponding substituents of a compound of formula (III).

The following Examples illustrate, but do not limit, the invention.

PREPARATION EXAMPLES

1. Reactions of Type (1)

Example 1.1

Preparation of 3-sulfinylamino-benzoyl chloride

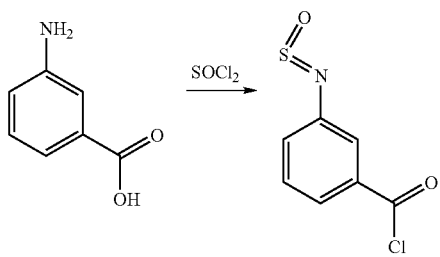 [SMILES: Nc1cccc(C(=O)O)c1 ; "SOCl2" ; O=S=Nc1cccc(C(=O)Cl)c1]

Thionyl chloride (95.17 g, 0.8 mol) was added to a solution of 3-amino-benzoic acid (27.43 g, 0.2 mol) in toluene (250 ml). The reaction mixture was heated to reflux for 2 hours. Excess thionyl chloride and toluene were distilled off under reduced pressure. The purification of the residue was performed by bulb-to-bulb distillation at 167° C. under vacuum (0.40 mbar) to give 3-sulfinylamino-benzoyl chloride (29.6 g, 73.4% yield).

Example 1.2

Preparation of 3-sulfinylamino-4-bromo-benzoyl chloride

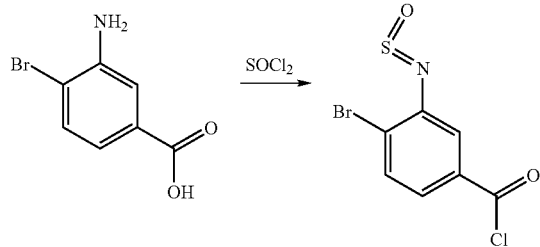 [SMILES: Nc1cc(C(=O)O)ccc1Br ; "SOCl2" ; O=S=Nc1cc(C(=O)Cl)ccc1Br]

Thionyl chloride (4.4 g, 37 mmol) was added to a solution of 3-amino-4-bromo-benzoic acid (2 g, 9.25 mmol) in toluene (12 ml). The reaction mixture was heated to reflux for 2 hours. Excess thionyl chloride and toluene were distilled off under reduced pressure. The purification of the residue was performed by bulb-to-bulb distillation at 130° C. under vacuum (0.40 mbar) to give 3-sulfinylamino-4-bromo-benzoyl chloride (0.978 g, 48.9% yield).

Example 1.3

Preparation of 3-sulfinylamino-4-cyano-benzoyl chloride

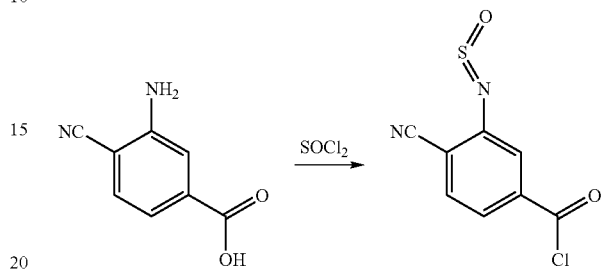

Thionyl chloride (4.4 g, 37 mmol) was added to a solution of 3-amino-4-cyano-benzoic acid (2.0 g, 9.25 mmol) (Example 6.1) in toluene (12 ml). The reaction mixture was heated to reflux for 2 hours. Excess thionyl chloride and toluene were distilled off under reduced pressure. The product was used without further purification.

2. Reactions of Type (2)

Example 2.1

Preparation of 3-sulfinylamino-N-[2-ethyl-6-methyl-4-(1,2,2,2-tetrafluoro-1-trifluoromethyl-ethyl)-phenyl]-benzamide

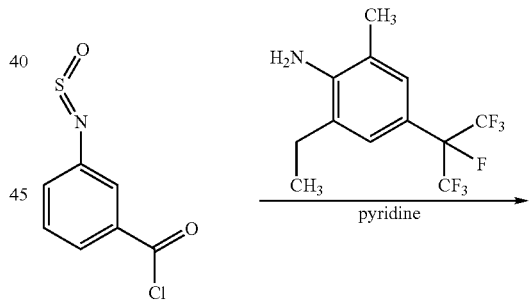

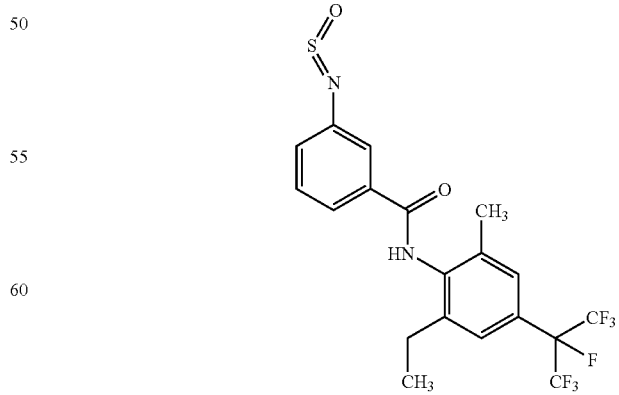

To a solution of 3-sulfinylamino-benzoyl chloride (0.033 g, 0.165 mmol) (Example 1.1) in dry deuterochloroform (0.5 ml) was added under stirring at 25° C., a solution of 2-ethyl-6-methyl-4-(1,2,2,2-tetrafluoro-1-trifluoromethyl-ethyl)-phenylamine (0.050 g, 0.165 mmol) (prepared according to EP 1,006,102) in deuterochloroform (0.5 ml). After stirring for 14 hours at 40° C., pyridine (0.013 g, 0.16 mmol) was added to the reaction mixture, followed by stirring for 60 hours at 25° C. An aliquot of the reaction mixture was diluted in dry acetonitrile and was submitted to mass spectrometry via direct injection (see conditions below). Calculated exact mass: 468; [M-H]⁻ observed: 467.01.

Mass spectrometric analysis: direct injection with solvent acetonitrile. Injection flow was 5 μl/min. Mass spectrometric detection was performed on a Quattro Micro triple quadrupole mass spectrometer (Waters).

| Scan Mode: | Quadrupole Scan | |
|---|---|---|
| MS Technique: | Electrospray Ionisation (ESI) | |
| Ion Mode: | Positive ions | Negative ions |
| Capillary Voltage: | 3.2 kV | 3.2 kV |
| Cone Voltage: | 20 V | 30 V |
| Desolvation Temperature: | 350° C. | 350° C. |
| Source Block Temp.: | 120° C. | 120° C. |
| Desolvation Gas Flow: | 500 L/h | 500 l/h |
| Cone Gas Flow: | 50 L/h | OFF |
| Scan Range: | 100 to 1000 Da | 100 to 1000 Da |
| Scan Time: | 0.5 sec | 0.5 sec |

Example 2.2

Alternative preparation of 3-sulfinylamino-N-[2-ethyl-6-methyl-4-(1,2,2,2-tetrafluoro-1-trifluoromethyl-ethyl)-phenyl]-benzamide

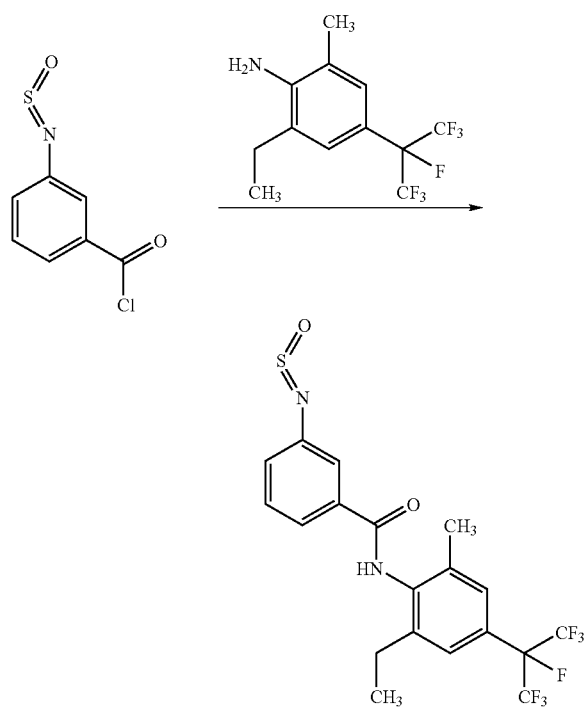

To a solution of 3-sulfinylamino-benzoyl chloride (0.033 g, 0.165 mmol) (Example 1.1) in dry deuterochloroform (0.5 ml) was added under stirring at 25° C., a solution of 2-ethyl-6-methyl-4-(1,2,2,2-tetrafluoro-1-trifluoromethyl-ethyl)-phenylamine (0.050 g, 0.165 mmol) (prepared according to EP 1,006,102) in deuterochloroform (0.5 ml). After stirring for 60 hours at 25° C., a sample of the reaction mixture was submitted to ¹H-NMR spectroscopy. The desired compound was detected in the reaction mixture together with unreacted starting materials. Integration of the signals showed a conversion of 40%. ¹H-NMR (CDCl₃, 400 MHz): 8.35 (s, 1H), 8.07 (d, 1H), 7.95 (d, 1H) 7.58 (t, 1H), 7.49 (s, 1H), 7.37 (s, 2H), 2.70 (q, 2H), 2.31 (s, 3H), 1.22 (t, 3H) ppm.

Example 2.3

Alternative preparation of 3-sulfinylamino-N-[2-ethyl-6-methyl-4-(1,2,2,2-tetrafluoro-1-trifluoromethyl-ethyl)-phenyl]-benzamide

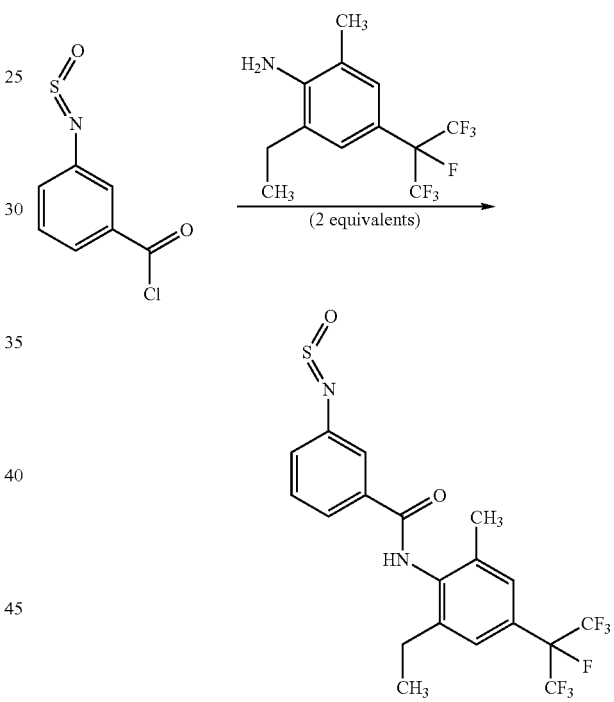

To a solution of 2-ethyl-6-methyl-4-(1,2,2,2-tetrafluoro-1-trifluoromethyl-ethyl)-phenylamine (0.100 g, 0.33 mmol) (prepared according to EP 1,006,102) in deuterochloroform (1.0 ml) was added under stirring at 25° C., a solution of 3-sulfinylamino-benzoyl chloride (0.033 g, 0.165 mmol) (Example 1.1) in dry deuterochloroform (1.0 ml). After stirring for 8 hours at 40° C., a sample of the reaction mixture was submitted to ¹H-NMR spectroscopy. The desired compound was detected in the reaction mixture, based on its characteristic signals (see ¹H-NMR spectral data as described in Example 2.2), together with unreacted starting materials. Integration of the signals showed a conversion of 85%. An aliquot of the reaction mixture was diluted in dry acetonitrile and was submitted to mass spectrometry via direct injection (same conditions as described in Example 2.1). Calculated exact mass: 468; [M-H]⁻ observed: 467.06.

Example 2.4

Alternative preparation of 3-sulfinylamino-N-[2-ethyl-6-methyl-4-(1,2,2,2-tetrafluoro-1-trifluoromethyl-ethyl)-phenyl]-benzamide

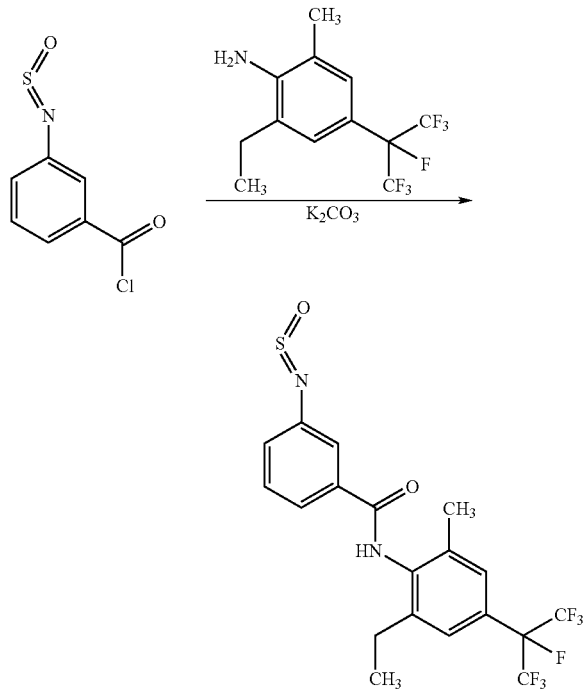

To a suspension of 2-ethyl-6-methyl-4-(1,2,2,2-tetrafluoro-1-trifluoromethyl-ethyl)-phenylamine (0.082 g, 0.27 mmol) (prepared according to EP 1,006,102) and finely ground potassium carbonate (0.112 g, 0.81 mmol) in deuterochloroform (1.0 ml) under stirring at 25° C., was added 3-sulfinylamino-benzoyl chloride (0.055 g, 0.27 mmol) (Example 1.1) dissolved in dry deuterochloroform (1.0 ml). The reaction mixture was stirred at 40° C. for 16 hours. A sample of the supernatant was submitted to $^1$H-NMR spectroscopy. The desired compound was detected in the reaction mixture, based on its characteristic signals (see $^1$H-NMR spectral data as described in Example 2.2), together with unreacted starting materials. An aliquot of the reaction mixture was diluted in dry acetonitrile and was submitted to mass spectrometry via direct injection (same conditions as described in Example 2.1). Calculated exact mass: 468; [M-H]$^-$ observed: 467.00.

3. Reactions of Type (3)

Example 3.1

Preparation of 3-amino-N-[2-ethyl-6-methyl-4-(1,2,2,2-tetrafluoro-1-trifluoromethyl-ethyl)-phenyl]-benzamide

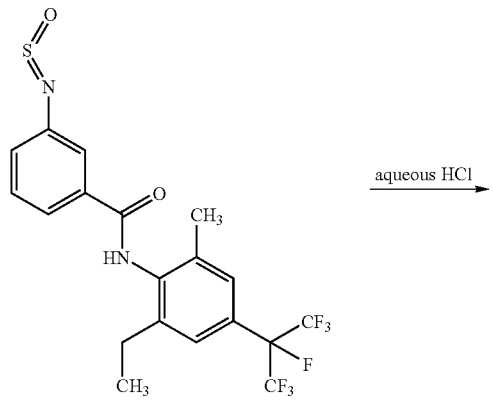

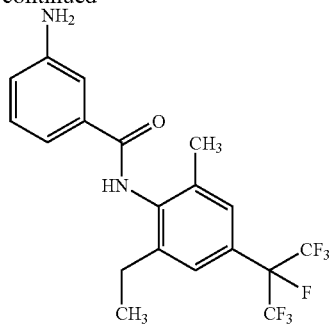

A solution of 3-sulfinylamino-N-[2-ethyl-6-methyl-4-(1,2,2,2-tetrafluoro-1-trifluoromethyl-ethyl)-phenyl]-benzamide (0.111 g, 0.237 mmol) (for example, Example 2.1) in dichloromethane (2 ml) and tetrahydrofuran (2 ml) was treated with aqueous hydrochloric acid (2N) (1 ml) and stirred at 25° C. for 30 minutes. The organic solvents were removed from the reaction mixture under reduced pressure. The residue was neutralized with aqueous sodium hydrogen carbonate (saturated) and was extracted with dichloromethane. The organic phase was dried over sodium sulfate and evaporated to yield the desired compound. $^1$H-NMR (CDCl$_3$, 400 MHz): 7.44 (s, 1H), 7.38 (s, 2H), 7.30-7.20 (m, 3H), 6.89 (d, 1H), 3.85 (bs, 2H), 2.69 (q, 2H), 2.32 (s, 3H), 1.22 (t, 3H) ppm.

4. Reactions of Type (4)

Example 4.1

Alternative preparation of 3-amino-N-[2-ethyl-6-methyl-4-(1,2,2,2-tetrafluoro-1-trifluoromethyl-ethyl)-phenyl]-benzamide

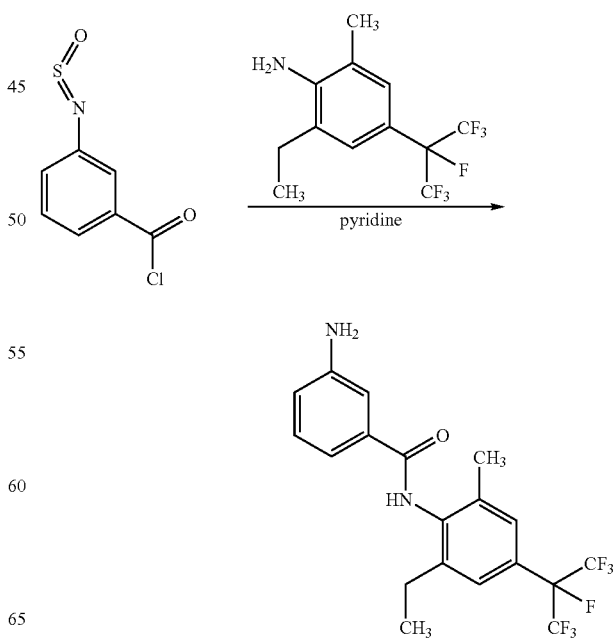

To a solution of 2-ethyl-6-methyl-4-(1,2,2,2-tetrafluoro-1-trifluoromethyl-ethyl)-phenylamine (2.09 g, 6.9 mmol) (prepared according to EP 1,006,102) in dichloromethane (30 ml) under stirring at 25° C., was added sequentially pyridine (0.8 ml, 9.9 mmol) and a solution of 3-sulfinylamino-benzoyl chloride (1.39 g, 6.9 mmol) (Example 1.1) in dichloromethane (7 ml). The reaction mixture was stirred at ambient temperature for 6 hours. The reaction mixture was quenched by addition of aqueous hydrochloric acid (2N) (4 ml) and stirred vigorously for 20 minutes. The mixture was diluted with water (20 ml) and the phases separated. The aqueous phase was extracted twice with ethyl acetate. The combined organic phases were washed successively with aqueous sodium hydrogen carbonate (saturated) and brine, dried over sodium sulfate and concentrated. The residue was purified by column chromatography on silica gel (eluent: ethyl acetate/cyclohexane 1:4 to 3:2). After evaporation of the solvents, the yellow oil was triturated with hexane, where it crystallized. The desired compound was isolated as white crystals. M.p. 143-145° C. $^1$H-NMR as described for Example 3.1.

Example 4.2

Preparation of 3-amino-N-[2-methyl-4-(1,2,2,2-tetrafluoro-1-trifluoromethyl-ethyl)-6-thiocyanato-phenyl]-benzamide

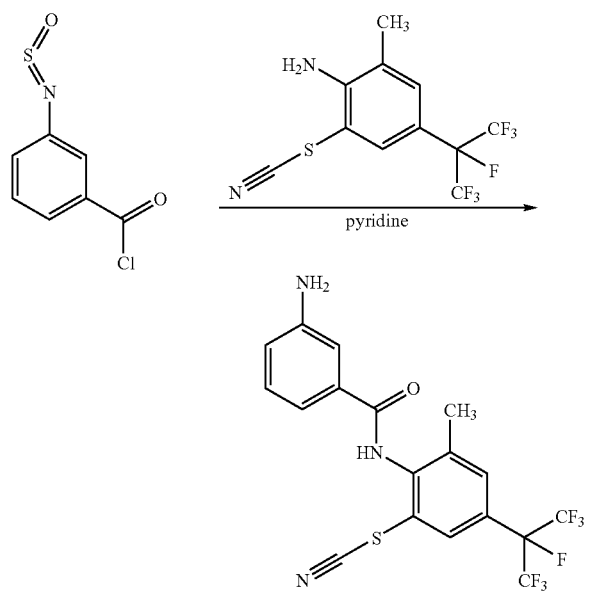

To a solution of 2-methyl-4-(1,2,2,2-tetrafluoro-1-trifluoromethyl-ethyl)-6-thiocyanate-phenylamine (3.00 g, 9.05 mmol) (Example 6.2) in anhydrous dichloromethane (80 ml), at 20° C., was added sequentially a solution of 3-sulfinylamino-benzoyl chloride (2.74 g, 13.58 mmol) (Example 1.1) in anhydrous dichloromethane (10 ml) and a solution of pyridine (2.15 g, 27.15 mmol) in anhydrous dichloromethane (10 ml). The reaction mixture was stirred at ambient temperature for one hour. The reaction mixture was quenched by addition of water (50 ml). After separation of the phases, the aqueous layer was extracted with dichloromethane. The combined organic phases were dried over sodium sulfate and concentrated. The residue was purified by column chromatography on silica gel (eluent: ethyl acetate/cyclohexane 2:3) to give 3-amino-N-[2-methyl-4-(1,2,2,2-tetrafluoro-1-trifluoromethyl-ethyl)-6-thiocyanato-phenyl]-benzamide (2.3 g, 56.3% yield). $^1$H-NMR (CDCl$_3$, 400 MHz): 7.95 (s, 1H), 7.45 (s, 1H), 7.29-7.28 (m, 3H), 6.92 (m, 1H), 5.73 (s, 2H), 2.59 (s, 6H) ppm.

Example 4.3

Preparation of 3-amino-4-bromo-N-[2,6-dimethyl-4-(1,2,2,2-tetrafluoro-1-trifluoromethyl-ethyl)-phenyl]-benzamide

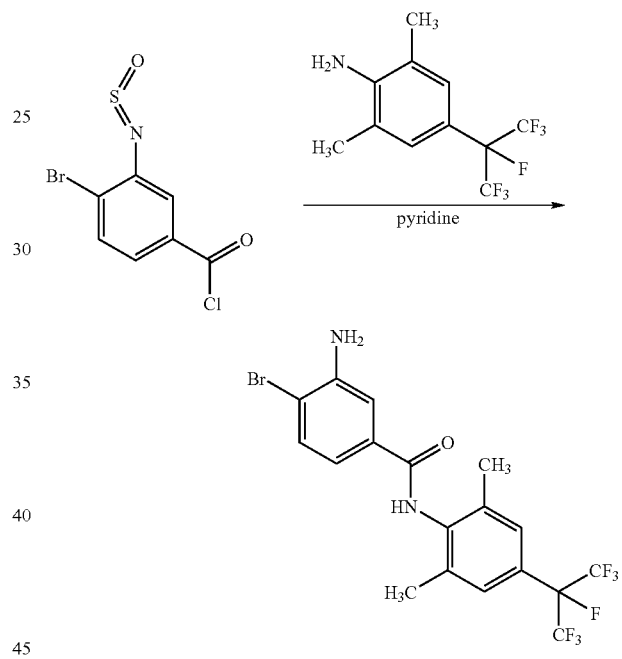

To a solution of 2,6-dimethyl-4-(1,2,2,2-tetrafluoro-1-trifluoromethyl-ethyl)-phenylamine (0.31 g, 1.1 mmol) (prepared according to EP 1,006,102) in anhydrous tetrahydrofuran (2 ml), at 20° C., was added sequentially pyridine (0.174 g, 2.2 mmol) and a solution of 3-sulfinylamino-benzoyl chloride (0.25 g, 0.86 mmol) (Example 1.2) in anhydrous tetrahydrofuran (2 ml). The reaction mixture was stirred at ambient temperature for three hours. The reaction mixture was quenched by addition of water (5 ml). After separation of the phases, the aqueous layer was extracted with ethyl acetate. The combined organic phases were dried over sodium sulfate and concentrated. The residue was purified by column chromatography on silica gel (eluent: ethyl acetate/cyclohexane 1:3) to give 3-amino-4-bromo-N-[2,6-dimethyl-4-(1,2,2,2-tetrafluoro-1-trifluoromethyl-ethyl)-phenyl]-benzamide (0.235 g, 78% yield). $^1$H-NMR (DMSO-d$_6$, 400 MHz): 7.53 (d, 1H), 7.44 (s, 2H), 7.38 (d, 1H), 7.10 (q, 1H), 5.6 (s, 2H), 2.24 (s, 6H) ppm.

Example 4.4

Preparation of 3-amino-4-bromo-N-[2,6-dichloro-4-(1,2,2,2-tetrafluoro-1-trifluoromethyl-ethyl)-phenyl]-benzamide

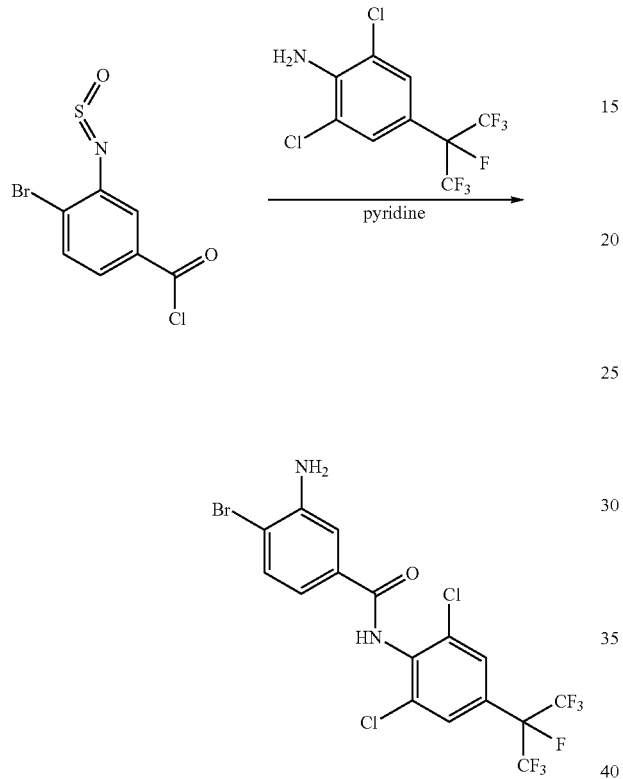

To a solution of 2,6-dichloro-4-(1,2,2,2-tetrafluoro-1-trifluoromethyl-ethyl)-phenylamine (1.02 g, 3.1 mmol) (Example 6.3) in anhydrous dichloromethane (25 ml), at 20° C., was added sequentially pyridine (0.74 g, 2.0 mmol) and 4-bromo-3-sulfinylamino-benzoyl chloride (0.94 g, 9.30 mmol) (Example 1.2). The reaction mixture was stirred at ambient temperature for one hour. The reaction mixture was then heated to 50° C. for 16 hours. The reaction mixture was allowed to cool to ambient temperature before adding dimethylformamide (50 ml). The dichloromethane was distilled off and the reaction mixture was heated to 130° C. for 16 hours. The reaction was quenched by addition of aqueous sodium hydrogen carbonate (saturated) (10 ml). After separation of the phases, the aqueous layer was extracted with ethyl acetate. The combined organic phases were dried over sodium sulfate and concentrated. The residue was purified by column chromatography on silica gel (eluent: ethyl acetate/cyclohexane 1:5 to 1:0) to give 3-amino-4-bromo-N-[2,6-dimethyl-4-(1,2,2,2-tetrafluoro-1-trifluoromethyl-ethyl)-phenyl]-benzamide (quantitative, 100% yield). $^1$H-NMR (CDCl$_3$, 400 MHz): 7.73 (m, 3H), 7.27 (m, 3H), 6.91 (m, 1H), 3.9 (s, 2H) ppm.

Example 4.5

Preparation of 3-amino-4-cyano-N-[2,6-dimethyl-4-(1,2,2,2-tetrafluoro-1-trifluoromethyl-ethyl)-phenyl]-benzamide

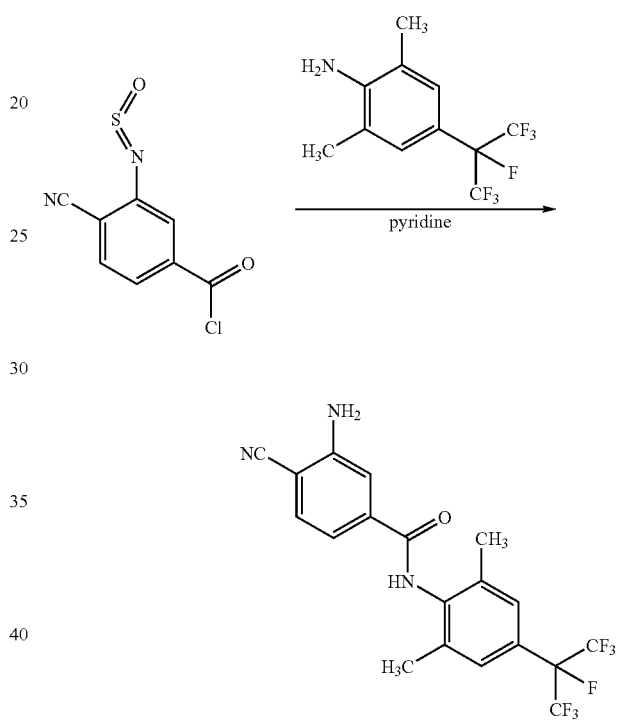

To a solution of 2,6-dimethyl-4-(1,2,2,2-tetrafluoro-1-trifluoromethyl-ethyl)-phenylamine (0.19 g, 0.69 mmol) (prepared according to EP 1,006,102) in tetrahydrofuran (3 ml), at 20° C., was added sequentially pyridine (0.145 g, 1.84 mmol) and a solution of 3-sulfinylamino-4-cyano-benzoyl chloride (0.150 g, 0.92 mmol) (Example 1.3). After two hours, the reaction mixture was quenched by addition of a mixture of aqueous potassium hydrogen carbonate (saturated) and water (1:1, 10 ml). After separation of the phases, the aqueous layer was extracted with ethyl acetate. The organic phases were dried over sodium sulfate and concentrated. The residue was purified by column chromatography on silica gel (eluent: ethyl acetate/cyclohexane 1:1 to 1:0) to give 3-amino-4-cyano-N-[2,6-dimethyl-4-(1,2,2,2-tetrafluoro-1-trifluoro-methyl-ethyl)-phenyl]-benzamide (0.049 g, 16.4% yield). $^1$H-NMR (CDCl$_3$, 400 MHz): 7.54 (s, 1H), 7.49 (d, 2H), 7.36 (m, 3H), 7.15 (q, 1H), 2.3 (s, 6H) ppm.

5. Reactions of Type (5)

Example 5.1

Alternative preparation of 3-sulfinylamino-N-[2-ethyl-6-methyl-4-(1,2,2,2-tetrafluoro-1-trifluoromethyl-ethyl)-phenyl]-benzamide

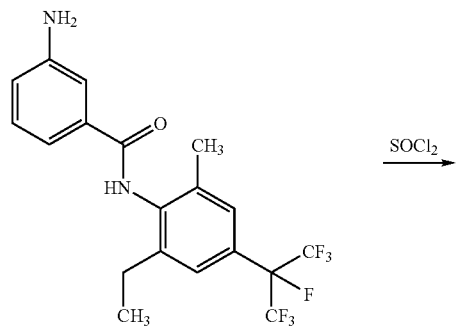

A suspension of 3-amino-N-[2-ethyl-6-methyl-4-(1,2,2,2-tetrafluoro-1-trifluoromethyl-ethyl)-phenyl]-benzamide (0.100 g, 0.237 mmol) (Example 4.1) in carbon tetrachloride (1 ml) was heated to 50° C. until it became a clear solution. A solution of thionyl chloride in carbon tetrachloride (1.68 M) (0.725 ml, 1.218 mmol) was added and the mixture was heated to 80° C. for one hour. The reaction mixture was evaporated under reduced pressure and the residue was triturated with cyclohexane. The suspension was filtered and the solid dried under high vacuum. The desired compound was obtained as white crystals. M.p. 100-108° C. $^1$H-NMR as described for Example 2.2. Mass spectrometric analysis: conditions as described for Example 2.1. Calculated exact mass: 468; [M-H]$^-$ observed: 467.06.

6. Synthesis of Intermediates

Example 6.1

Preparation of 3-amino-4-cyano-benzoic acid

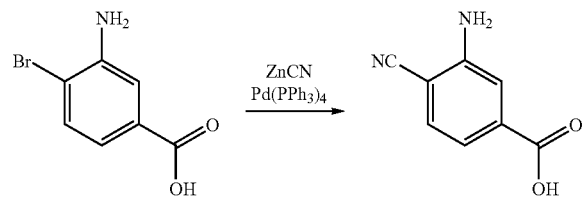

To a solution of 3-amino-4-bromo-benzoic acid (6.0 g, 276 mmol) in dimethyl formamide (30 ml), was added sequentially at ambient temperature zinc cyanide (11.66 g, 99.4 mmol) and tetrakis(triphenylphosphine)palladium (9.57 g, 8.28 mmol). The mixture was heated to 100° C. for 14 hours. The reaction mixture was allowed to cool to ambient temperature before the sequential addition of more zinc cyanide (0.65 g, 5.54 mmol) and tetrakis(triphenylphosphine)palladium (1.9 g, 1.64 mmol) at ambient temperature. The mixture was heated to 100° C. for 1 more hour. The reaction mixture was allowed to cool to ambient temperature and was quenched by addition of a mixture of toluene and aqueous ammonia (1M). The phases were separated and the aqueous layer was extracted with toluene. The combined organic phases were dried over sodium sulfate and concentrated. The residue was purified by column chromatography on silica gel (eluent: ethyl acetate/cyclohexane 1:2 to 1:0) to give 3-amino-4-cyano-benzoic acid (2.94 g, 67% yield).

Example 6.2

Preparation of 2-methyl-4-(1,2,2,2-tetrafluoro-1-trifluoromethyl-ethyl)-6-thiocyanato-phenylamine

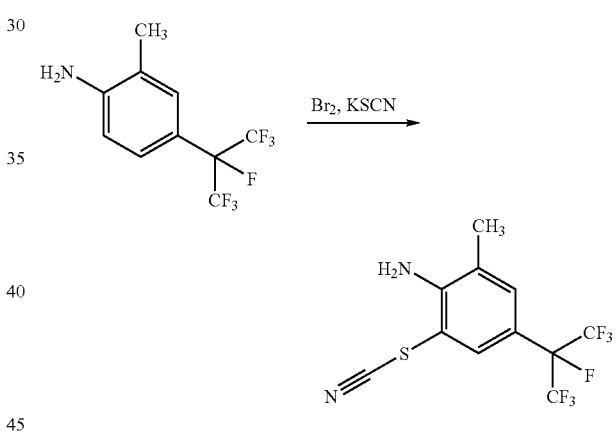

To a solution of 2-methyl-4-(1,2,2,2-tetrafluoro-1-trifluoromethyl-ethyl)-phenylamine (5.0 g, 18.20 mmol) (prepared according to EP 1,006,102) in acetic acid (30 ml) was added a solution of potassium thiocyanate (7.25 g, 74.62 mmol) in acetic acid (20 ml). The solution was cooled to 5° C. before the addition of bromine (3.2 g, 1.03 ml) in acetic acid (10 ml). The reaction mixture was allowed to warm to ambient temperature and was stirred at ambient temperature for 3 hours. The reaction mixture was quenched by pouring into water. The mixture was extracted with ethyl acetate (3×100 ml). The combined organic extracts were washed successively with aqueous sodium hydroxide (10 g/l) (100 ml), water (100 ml) and brine (100 ml), dried over sodium sulfate and concentrated. The residue was purified by column chromatography on silica gel (eluent: ethyl acetate/cyclohexane 1:3) to give 2-methyl-4-(1,2,2,2-tetrafluoro-1-trifluoromethyl-ethyl)-6-thiocyanato-phenylamine (3.7 g, 61.2% yield). $^1$H-NMR (CDCl$_3$, 400 MHz): 7.68 (s, 1H), 7.33 (s, 1H), 5.73 (s, 2H), 2.59 (s, 6H) ppm.

Example 6.3

Preparation of 2,6-dichloro-4-(1,2,2,2-tetrafluoro-1-trifluoromethyl-ethyl)-phenylamine To a solution of 4-(1,2,2,2-tetrafluoro-1-trifluoromethyl-ethyl)-phenylamine (10 g, 38.30 mmol) (prepared according to EP 1,006,102) in dichloromethane (150 ml), at 20° C., was added N-chlorosuccinimide ("NCS") (21.48 g, 160.8 mmol). The reaction mixture was stirred overnight at ambient temperature. The reaction was quenched by addition of aqueous sodium hydroxide (2N) and the phases were separated. The aqueous layer was extracted with dichloromethane. The combined organic phases were dried over sodium sulfate and concentrated. The residue was purified by column chromatography on silica gel (eluent: ethyl acetate/cyclohexane 1:4) to give 2,6-dichloro-4-(1,2,2,2-tetrafluoro-1-trifluoromethyl-ethyl)-phenylamine (7.6 g, 60.1% yield). $^1$H-NMR (CDCl$_3$, 400 MHz): 7.41 (s, 2H), 4.77 (s, 2H) ppm.

The invention claimed is:

1. A method of using an intermediate in the production of a compound of formula (IV)

wherein
$A^1, A^2, A^3$ and $A^4$ are independently of one another C—R$^3$ or nitrogen, provided that no more than two of $A^1, A^2, A^3$ and $A^4$ are nitrogen;

R$^2$ is hydrogen, C$_1$-C$_4$alkyl or C$_1$-C$_4$alkylcarbonyl-;

G$^2$ is oxygen or sulfur;

each R$^3$ is independently hydrogen, halogen, cyano, nitro, C$_1$-C$_4$alkyl, C$_1$-C$_4$haloalkyl, hydroxy, C$_1$-C$_4$alkoxy-, C$_1$-C$_4$haloalkoxy-, thiol, C$_1$-C$_4$alkylthio-, C$_1$-C$_4$haloalkylthio-, C$_1$-C$_4$alkylsulfinyl-, C$_1$-C$_4$haloalkylsulfinyl-, C$_1$-C$_4$alkylsulfonyl-, C$_1$-C$_4$haloalkylsulfonyl-, amino, N—C$_1$-C$_4$alkylamino- or N,N-di-(C$_1$-C$_4$alkyl)-amino-; and Q$^2$ is a moiety of formula (A) or (B)

wherein
Y$^1$ and Y$^5$ are independently of each other halogen, cyano, thiocyanato, C$_1$-C$_4$alkyl, C$_1$-C$_4$haloalkyl, C$_1$-C$_4$alkoxy-C$_1$-C$_4$-alkyl-, cyano-C$_1$-C$_4$-alkyl-, C$_1$-C$_3$alkylthio-, C$_1$-C$_3$haloalkylthio-, C$_1$-C$_3$alkylsulfinyl-, C$_1$-C$_3$haloalkylsulfinyl-, C$_1$-C$_3$alkylsulfonyl- or C$_1$-C$_3$haloalkylsulfonyl-;

Y$^3$ is C$_2$-C$_6$perfluoroalkyl, C$_1$-C$_6$perfluoroalkylthio-, C$_1$-C$_6$perfluoroalkylsulfinyl- or C$_1$-C$_6$perfluoroalkylsulfonyl-;

Y$^2$ and Y$^4$ are independently of each other hydrogen, halogen or C$_1$-C$_4$alkyl;

Y$^6$ and Y$^9$ are independently of each other halogen, cyano, thiocyanato, C$_1$-C$_4$alkyl, C$_1$-C$_4$haloalkyl, C$_1$-C$_4$alkoxy-C$_1$-C$_4$-alkyl-, cyano-C$_1$-C$_4$-alkyl-, C$_1$-C$_3$alkylthio-, C$_1$-C$_3$haloalkylthio-, C$_1$-C$_3$alkylsulfinyl-, C$_1$-C$_3$haloalkylsulfinyl-, C$_1$-C$_3$alkylsulfonyl- or C$_1$-C$_3$haloalkylsulfonyl-;

Y$^8$ is C$_1$-C$_4$haloalkoxy-, C$_2$-C$_6$perfluoroalkyl, C$_1$-C$_6$perfluoroalkylthio-, C$_1$-C$_6$perfluoroalkylsulfinyl- or C$_1$-C$_6$perfluoroalkylsulfonyl-; and Y$^7$ is hydrogen, halogen or C$_1$-C$_4$alkyl;

or an N-oxide or a salt thereof;

wherein:
a) the intermediate comprises a compound of formula (I)

or an N-oxide or a salt thereof, and said method comprises (i) treating the compound of formula (I) with thionyl chloride in the presence of an aprotic solvent to form a compound of formula (II)

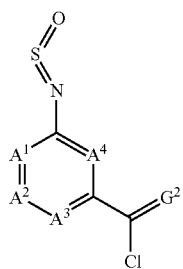

(II)

or an N-oxide or a salt thereof, followed by (ii) treatment of the compound of formula (II) with an amine of formula $HNR^2Q^2$, under basic conditions, forming a compound of formula (III)

(III)

or an N-oxide or a salt thereof, followed by (iii) treating the compound of formula (III) with water; or b) the intermediate comprises a compound of formula (II)

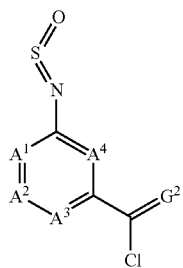

(II)

or an N-oxide or a salt thereof, and said method comprises (i) treating the compound of formula (II) with an amine of formula $HNR^2Q^2$, under basic conditions, forming a compound of formula (III)

(III)

or an N-oxide or a salt thereof, followed by (ii) treating the compound of formula (III) with water; or c) the intermediate comprises a compound of formula (III)

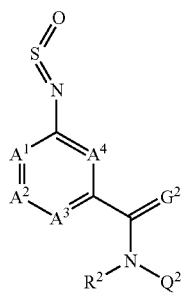

(III)

or an N-oxide or a salt thereof, and said method comprises treating the compound of formula (III) with water.

2. A method of preparing a compound of formula (III)

(III)

wherein $A^1$, $A^2$, $A^3$, $A^4$, $R^2$, $G^2$ and $Q^2$ are as defined in claim 1, said method comprising treating a compound of formula (II)

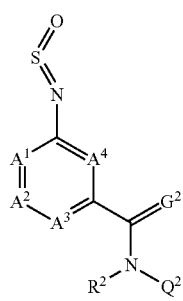

(II)

with an amine of formula $HNR^2Q^2$ under basic conditions.

3. A method of preparing a compound of formula (IV)

(IV)

wherein $A^1$, $A^2$, $A^3$, $A^4$, $R^2$, $G^2$ and $Q^2$ are as defined in claim 1, said method comprising treating a compound of formula (III)

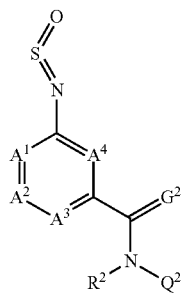

(III)

with water.

4. A method of preparing a compound of formula (IV)

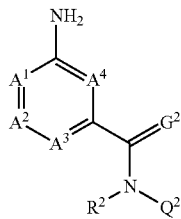

(IV)

wherein $A^1, A^2, A^3, A^4, R^2, G^2$ and $Q^2$ are as defined in claim 1, said method comprising treating a compound of formula (II)

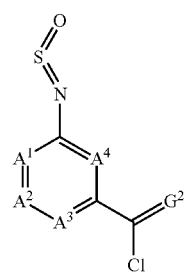

(II)

with an amine of formula $HNR^2Q^2$ under basic conditions, to form the compound of formula (III), followed by treatment of the compound of formula (III) with water.

5. A compound of formula (II')

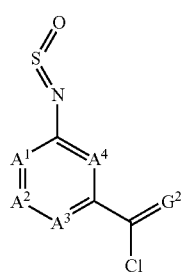

(II')

wherein $A^1, A^2, A^3, A^4$ and $G^2$ are as defined in claim 1; or an N-oxide or a salt thereof, provided that (II') is not 2-chloro-5-sulfinylamino-benzoyl chloride, 4-methoxy-3-sulfinylamino-benzoyl chloride, 4-methyl-3-sulfinylamino-benzoyl chloride, 3-sulfinylamino-benzoyl chloride, 2,3,4,6-tetraiodo-5-sulfinylamino-benzoyl chloride or 2,4,6-triiodo-3-sulfinylamino-benzoyl chloride.

6. A compound of formula (III')

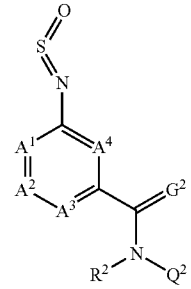

(III')

wherein $A^1, A^2, A^3, A^4, R^2, G^2$ and $Q^2$ are as defined in claim 1; or an N-oxide or a salt thereof.

7. The method of claim 1, wherein said step of treating the compound of formula (III) with water comprises treating the compound of formula (III) with water in an aprotic solvent.

8. A method of preparing a compound of formula (IV)

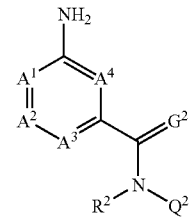

(IV)

wherein $A^1, A^2, A^3$ and $A^4$ are independently of one another C—$R^3$ or nitrogen, provided that no more than two of $A^1, A^2, A^3$ and $A^4$ are nitrogen;

$R^2$ is hydrogen, $C_1$-$C_4$alkyl or $C_1$-$C_4$alkylcarbonyl-;

$G^2$ is oxygen or sulfur;

each $R^3$ is independently hydrogen, halogen, cyano, nitro, $C_1$-$C_4$alkyl, $C_1$-$C_4$haloalkyl, hydroxy, $C_1$-$C_4$alkoxy-, $C_1$-$C_4$haloalkoxy-, thiol, $C_1$-$C_4$alkylthio-, $C_1$-$C_4$haloalkylthio-, $C_1$-$C_4$alkylsulfinyl-, $C_1$-$C_4$haloalkylsulfinyl-, $C_1$-$C_4$alkylsulfonyl-, $C_1$-$C_4$haloalkylsulfonyl-, amino, N—$C_1$-$C_4$alkylamino- or N,N-di-($C_1$-$C_4$alkyl)-amino-; and $Q^2$ is a moiety of formula (A) or (B)

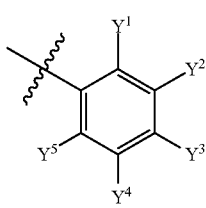

(A)

-continued

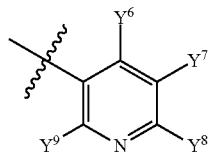
(B)

wherein
Y$^1$ and Y$^5$ are independently of each other halogen, cyano, thiocyanato, C$_1$-C$_4$alkyl, C$_1$-C$_4$haloalkyl, C$_1$-C$_4$alkoxy-C$_1$-C$_4$-alkyl-, cyano-C$_1$-C$_4$-alkyl-, C$_1$-C$_3$alkylthio-, C$_1$-C$_3$haloalkylthio-, C$_1$-C$_3$alkylsulfinyl-, C$_1$-C$_3$haloalkylsulfinyl-, C$_1$-C$_3$alkylsulfonyl- or C$_1$-C$_3$haloalkylsulfonyl-;
Y$^3$ is C$_2$-C$_6$ perfluoroalkyl, C$_1$-C$_6$ perfluoroalkylthio-, C$_1$-C$_6$ perfluoroalkylsulfinyl- or C$_1$-C$_6$ perfluoroalkylsulfonyl-;
Y$^2$ and Y$^4$ are independently of each other hydrogen, halogen or C$_1$-C$_4$alkyl;
Y$^6$ and Y$^9$ are independently of each other halogen, cyano, thiocyanato, C$_1$-C$_4$alkyl, C$_1$-C$_4$haloalkyl, C$_1$-C$_4$alkoxy-C$_1$-C$_4$-alkyl-, cyano-C$_1$-C$_4$-alkyl-, C$_1$-C$_3$alkylthio-, C$_1$-C$_3$haloalkylthio-, C$_1$-C$_3$alkylsulfinyl-, C$_1$-C$_3$haloalkylsulfinyl-, C$_1$-C$_3$alkylsulfonyl- or C$_1$-C$_3$haloalkylsulfonyl-;
Y$^8$ is C$_1$-C$_4$haloalkoxy-, C$_2$-C$_6$ perfluoroalkyl, C$_1$-C$_6$ perfluoroalkylthio-, C$_1$-C$_6$ perfluoroalkylsulfinyl- or C$_1$-C$_6$ perfluoroalkylsulfonyl-; and
Y$^7$ is hydrogen, halogen or C$_1$-C$_4$alkyl;
or an N-oxide or a salt thereof;
said method comprising treating a compound of formula (III)

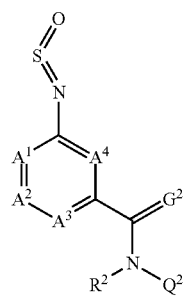
(III)

or an N-oxide or a salt thereof with water.

9. The method of claim 8, wherein said step of treating the compound of formula (III) with water comprises treating the compound of formula (III) with water in an aprotic solvent.

10. The method of claim 8, further comprising treating a compound of formula (II)

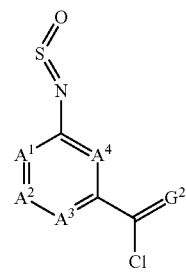
(II)

or an N-oxide or a salt thereof with an amine of formula HNR$^2$Q$^2$, under basic conditions, to form the compound of formula (III) or an N-oxide or a salt thereof.

11. The method of claim 10, further comprising treating a compound of formula (I)

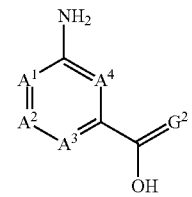
(I)

or an N-oxide or a salt thereof with thionyl chloride in the presence of an aprotic solvent to form a compound of formula (II) or an N-oxide or a salt thereof.

* * * * *